US012562264B2

(12) United States Patent
Tamarozzi et al.

(10) Patent No.: US 12,562,264 B2
(45) Date of Patent: Feb. 24, 2026

(54) METHOD FOR THE RECOMPOSITION OF A KIT OF SURGICAL INSTRUMENTS AND CORRESPONDING APPARATUS

(71) Applicant: PROMEDITAL S.R.L., Reggio nell'Emilia (IT)

(72) Inventors: Marco Tamarozzi, Modena (IT); Fiorenzo Pizza, San Benedetto del Tronto (IT); Riccardo Merolla, Castelnuovo né Monti (IT)

(73) Assignee: PROMEDITAL S.R.L., Reggio nell'Emilia (IT)

( * ) Notice: Subject to any disclaimer, the term of this patent is extended or adjusted under 35 U.S.C. 154(b) by 1037 days.

(21) Appl. No.: 17/638,416

(22) PCT Filed: Aug. 25, 2020

(86) PCT No.: PCT/IT2020/050209
§ 371 (c)(1),
(2) Date: Feb. 25, 2022

(87) PCT Pub. No.: WO2021/038610
PCT Pub. Date: Mar. 4, 2021

(65) Prior Publication Data
US 2022/0313388 A1 Oct. 6, 2022

(30) Foreign Application Priority Data
Aug. 27, 2019 (IT) ........................ 102019000015072

(51) Int. Cl.
*G06K 9/00* (2022.01)
*A61B 90/98* (2016.01)

*G06V 20/00* (2022.01)
*G16H 40/40* (2018.01)

(52) U.S. Cl.
CPC ............. *G16H 40/40* (2018.01); *A61B 90/98* (2016.02); *G06V 20/00* (2022.01); *G06V 2201/034* (2022.01)

(58) Field of Classification Search
CPC ........ G16H 40/40; A61B 90/98; G06V 20/00; G06V 2201/034
See application file for complete search history.

(56) References Cited

U.S. PATENT DOCUMENTS

| | | | |
|---|---|---|---|
| 10,617,478 B1 * | 4/2020 | Foster | A61B 90/90 |
| 12,141,733 B2 * | 11/2024 | Montano | G16H 40/20 |
| 2005/0038556 A1 * | 2/2005 | Gagnon | A61B 90/94 |
| | | | 700/226 |
| 2011/0005342 A1 * | 1/2011 | Treat | G16H 40/40 |
| | | | 414/754 |

(Continued)

OTHER PUBLICATIONS

International Search Report filed in PCT/IT2020/050209 dated Dec. 16, 2020.

*Primary Examiner* — Avinash Yentrapati
(74) *Attorney, Agent, or Firm* — RANKIN, HILL & CLARK LLP

(57) ABSTRACT

A method and an apparatus for the recomposition of a kit of surgical instruments is provided to dispose a plurality of surgical instruments on a support plane in a support device; to acquire an image of the surgical instruments by means of at least one optical detection device; and to recognize each surgical instrument by processing the acquired images.

6 Claims, 2 Drawing Sheets

(56)           References Cited

U.S. PATENT DOCUMENTS

| | | | |
|---|---|---|---|
| 2013/0091679 A1* | 4/2013 | Gloger | G16H 40/63 |
| | | | 29/407.04 |
| 2013/0164103 A1* | 6/2013 | Baker | G16H 20/40 |
| | | | 414/266 |
| 2013/0336554 A1* | 12/2013 | Lewis | G06F 16/90 |
| | | | 382/128 |
| 2015/0190202 A1* | 7/2015 | Weinert | A61B 90/98 |
| | | | 340/5.8 |
| 2016/0042130 A1* | 2/2016 | Broninx | G06F 16/2358 |
| | | | 705/2 |
| 2019/0290796 A1* | 9/2019 | Ma | G16H 40/20 |
| 2020/0143195 A1* | 5/2020 | Montano | G16H 40/20 |
| 2020/0168322 A1* | 5/2020 | Brandt | A61B 50/24 |

* cited by examiner

METHOD FOR THE RECOMPOSITION OF A KIT OF SURGICAL INSTRUMENTS AND CORRESPONDING APPARATUS

FIELD OF THE INVENTION

The present invention concerns a method for the recomposition of a kit of surgical instruments, formed by a plurality of instruments suitable to carry out a particular surgical operation, and a corresponding apparatus suitable to implement said method.

BACKGROUND OF THE INVENTION

In the health sector, for example in hospitals, or in general in any facility where operating theaters suitable for hosting surgical interventions are provided, it is necessary to manage the kits of instruments, each comprising a specific and determinate number and type of surgical instruments.

These instrument kits can be, for example, single-intervention procedural kits dedicated to a particular type of surgical intervention. In other words, for each specific intervention, the respective instrument kit will be present in the operating room.

At the end of each intervention, a reconditioning procedure is started for the surgical instruments comprised in the kit, in which the instruments are washed and sterilized, and possibly checked and maintained.

Subsequently, the kit has to be reconstituted by a specialized operator who checks the list of necessary instruments, takes them and places them in a container that contains the cleaned kit, ready to be used again in the operating room.

This operation to reassemble the kit is burdensome in terms of time, as many kits, even of a very different type from each other, can arrive from the operating theaters. The operator has to divide up the surgical instruments and identify each instrument that makes up the kit to be reconstructed. This operation is generally laborious and complex and requires a high degree of attention and concentration on the part of the operator.

Furthermore, the operator has to carry out a quality control on the instrument before putting it in the container, in order to identify possible non-conformities such as damaged, stained or still dirty parts.

The operation to reassemble the kit, in addition to being burdensome in terms of time, also entails a human error rate related to the correct identification of the surgical instrument from the list or resulting from the lack of identification of non-conformities. Therefore, this operation is generally carried out by trained and highly specialized personnel.

This is due to the fact that there are various types of kits consisting of a number of several dozen instruments, up to 150/200 instruments, possibly repeated inside the same kit, even similar in shape but differing in minimum details, such as for example a slight scale factor of certain parts of the instrument, which means that many instruments are easily confused with each other.

Moreover, in the environments where washing is carried out (dirty area), operators use gloves and individual protection devices, and consequently the use of instruments or keyboards is generally inconvenient and complicated. In addition, in the subsequent processing steps (packaging area), it is desired to limit as much as possible the handling of surgical instruments by the operators for hygienic/sanitary reasons.

In the hospital sector, therefore, the need to optimize the recognition process of surgical instruments, to certify they belong to the kits and to recognize possible non-conformities, is very much felt.

In the state of the art, methods are known to identify surgical instruments by affixing serial codes to the instrument.

For example, there are known methods that provide to engrave bar codes, such as qrcode or datamatrix, for example using laser or dot peen.

One disadvantage of these methods is their invasiveness, since they provide to engrave the code directly on the surface of the instrument itself, which entails numerous disadvantages.

Another disadvantage of these incision methods known in the state of the art is that the engraving could compromise the compliance of the instrument with the requirements necessary to qualify as a medical device, which is binding for use in the healthcare sector.

Another disadvantage of these methods is that the instrument can become unsafe, since dirt can accumulate in the zone where the incision takes place, or surface defects, such as rust, can occur.

Another disadvantage is that the engraving can at least partly fade with time, since the sterilization process can wear down the code, which over time becomes no longer legible.

Yet another disadvantage of these methods is that the code may also be difficult to affix, given that surgical instruments come in various sizes, shapes and materials. For example, in the case of very small instruments or instruments made of plastic material it may be difficult to affix the code on the instrument due to lack of space or due to the intrinsic nature of the material which is not suitable to be engraved with the techniques described above.

In such cases, the code affixed in this way can also be difficult to read, as it can be very small and therefore difficult to read with the instruments that are commonly available on the market, such as barcode readers for example.

Alternative methods, known in the state of the art, provide to affix RFID (Radio Frequency IDentification) devices instead of engraving the code on the instrument.

These methods, in addition to being subject to the same disadvantages as listed above with reference to barcode engraving, also have the additional disadvantage that the tag could detach from the instrument, even during a surgical intervention. This is to be avoided as it involves risks for the patient, in particular if the surgical team does not promptly notice the detachment.

Another disadvantage is that in some situations the reading of the tag can be difficult, for example due to signal shielding that can occur due to the well-known "Faraday cage" effect when surgical instruments are packaged or put in metal grids/containers.

Furthermore, in both types of methods known in the state of the art as described above, the marking step is a complex and expensive operation, which is usually carried out outside the hospital environment. However, in the case of pre-existing instruments, there is also the disadvantage related to the fact that removing surgical instruments from the hospital can lead to organizational difficulties, which entail a reorganization of the operating agenda, with the obvious inconvenience that ensues.

There is therefore a need to perfect a method for the recomposition of a kit of surgical instruments and a corresponding apparatus which can overcome at least one of the disadvantages of the state of the art.

One purpose of the invention is therefore to minimize human error and simultaneously reduce the recomposition time of the kit of surgical instruments, guiding the operators assigned to the method for recomposing the kit, following the reconditioning steps thereof.

Another purpose is to increase the safety and reliability of the method, for example by helping the operator to prepare complete kits, reducing the risk of noticing the lack of an instrument only later, at the moment when it is to be used, and also helping him/her to prepare correct kits, including exactly all the instruments required.

Another purpose is to allow better management of the surgical instruments, simplifying the maintenance and inventory operations of the surgical instruments of the hospital for the purposes of identifying and enhancing the stock inside the hospital or clinic, and a reduction in costs, for example for reducing working times and reducing non-conformities.

Another purpose is to make available a non-invasive method, which allows to avoid engraving or marking the instruments.

Another purpose is to perfect a method that allows to minimize the use of the operator's hands, limiting the need to use physical interfaces such as reading tools or keyboards.

Another purpose of the invention is also to help the operator to verify the conformity of the instruments, identifying possible defects, during the maintenance and quality control of the surgical instruments.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the present invention or variants to the main inventive idea.

In accordance with the above purposes, some embodiments described here concern a method for the recomposition of a kit of surgical instruments, comprising a plurality of instruments suitable to perform a particular surgical operation.

Some embodiments described below concern a method for the recomposition of a kit of surgical instruments in which it is provided to dispose a plurality of surgical instruments on a support plane comprised in a support device and acquire the images of such instruments by means of an optical detection device.

According to one characteristic aspect of the method according to the present invention, there is provided a step of recognizing the surgical instruments by processing the images acquired, in which the images acquired are compared with comparison images contained in a storage module, and a step of graphically displaying the outcome of the recognition step on a user interface.

According to some embodiments described here, the outcome of the recognition is positive if the acquired image can be at least partly superimposed on one of the images contained in the storage module with a level of confidence higher than a certain predefined threshold, for example equal to or greater than 80%, preferably equal to or greater than 90%.

In accordance with one form of implementation of the method according to the present invention, when such level of confidence is lower than the threshold as above, the outcome of the recognition step is negative and a selection step is provided, in which the operator can indicate which is the instrument being examined among a limited group of instruments on the basis of a graphic comparison proposed on a screen.

In an example form of embodiment, the selection step provides to show the operator an image of the instrument acquired by the optical detection devices and some windows, each representing a surgical instrument similar to the one visible in such image, together with the indication of a respective degree of compatibility, in particular expressed as a percentage, between the instrument visible in the respective window and the one shown in the acquired image.

According to some embodiments described here, the selection step provides to receive voice instructions from the operator, in particular to communicate the window containing the surgical instrument selected.

Some variants of the method according to the present invention provide to guide the operator in removing the surgical instruments from the support plane in order to insert them into a container intended to contain the kit as above according to a determinate sequence. In one example of implementation, the operator is guided by a light signal, emitted by one or several selection devices that selectively highlight the surgical instruments, one at a time, according to the preestablished sequential order.

According to another aspect of the present invention, an apparatus is made available for the recomposition of a kit of surgical instruments comprising a support device provided with a support plane for the surgical instruments, at least one optical detection device configured to acquire an image of the surgical instruments disposed on the support plane, a data processing system comprising a programmable central processing unit and a data storage module, wherein the data processing system is able to acquire data, in particular images, from the optical detection devices in order to process the data and recognize the surgical instruments by comparing the acquired image with comparison images contained in a storage module; the apparatus further comprising user interface devices provided with at least one screen to graphically display the outcome of the recognition.

According to some embodiments provided here, the apparatus comprises one or more devices to acquire instructions configured to receive instructions from an operator at least in a selection step in which the operator can indicate which is the instrument under examination among a limited group of instruments, on the basis of a graphic comparison proposed on the screen, the instruction acquisition devices being chosen in a group consisting of: microphone, keyboard, mouse, touch screen.

Thanks to the method and the apparatus for the recomposition of a kit of surgical instruments according to the present invention, it is advantageously possible to:

reduce the time needed to recompose kits, minimize human error in the recomposition process, in order to prevent incomplete kits or kits containing a wrong instrument instead of the correct one, prevent the need to intervene directly on the instruments with markings or affixing of codes, which allows to prevent the numerous inconveniences related to these operations according to the procedures known in the state of the art, make the recomposition method more reliable and safer even if it is not carried out by trained or highly specialized personnel, reduce the costs of managing kits of surgical instruments, thanks to the shorter time required for recomposition and the possibility of saving on personnel training costs.

This is achievable thanks to the steps of recognition and graphic display of surgical instruments, which allow to facilitate and speed up the operator's operations.

In fact, these steps can be implemented automatically while the operator is limited to supervising the functioning of the apparatus.

It should be noted that these advantageous effects also characterize the step of introducing the instruments into the container intended to contain the kit, since some embodiments described here provide to guide the operator in removing the instruments according to a preestablished sequential order, which allows to also make this step more efficient and rapid.

Other advantages are obtainable in the embodiments in which the operator interacts with the apparatus without any direct physical contact, for example thanks to the presence of a microphone comprised in the instruction acquisition devices through which the operator can give voice instructions, in particular in the selection step as above.

One advantage of these embodiments is to prevent, or minimize, the operator from using his/her hands in order to enter instructions in the devices to acquire instructions. In this way, the method is faster and more efficient, since the operator does not necessarily have to take off the gloves and personal protective equipment he/she wears in order to use a mouse and/or keyboards in order to enter instructions into the apparatus.

According to other aspects of the present invention, a computer-readable means and a computer program storable in a computer-readable means are made available, which both comprise instructions which, once executed by an apparatus according to the present invention, determine the execution of a method according to the present invention for the recomposition of a kit of surgical instruments.

These and other aspects, characteristics and advantages of the present disclosure will be better understood with reference to the following description, drawings and attached claims. The drawings, which are integrated and form part of the present description, show some embodiments of the present invention, and together with the description, are intended to describe the principles of the disclosure.

ILLUSTRATION OF THE DRAWINGS

These and other aspects, characteristics and advantages of the present invention will become apparent from the following description of some embodiments, given as a non-restrictive example with reference to the attached drawings wherein.

Figures 1, 2:
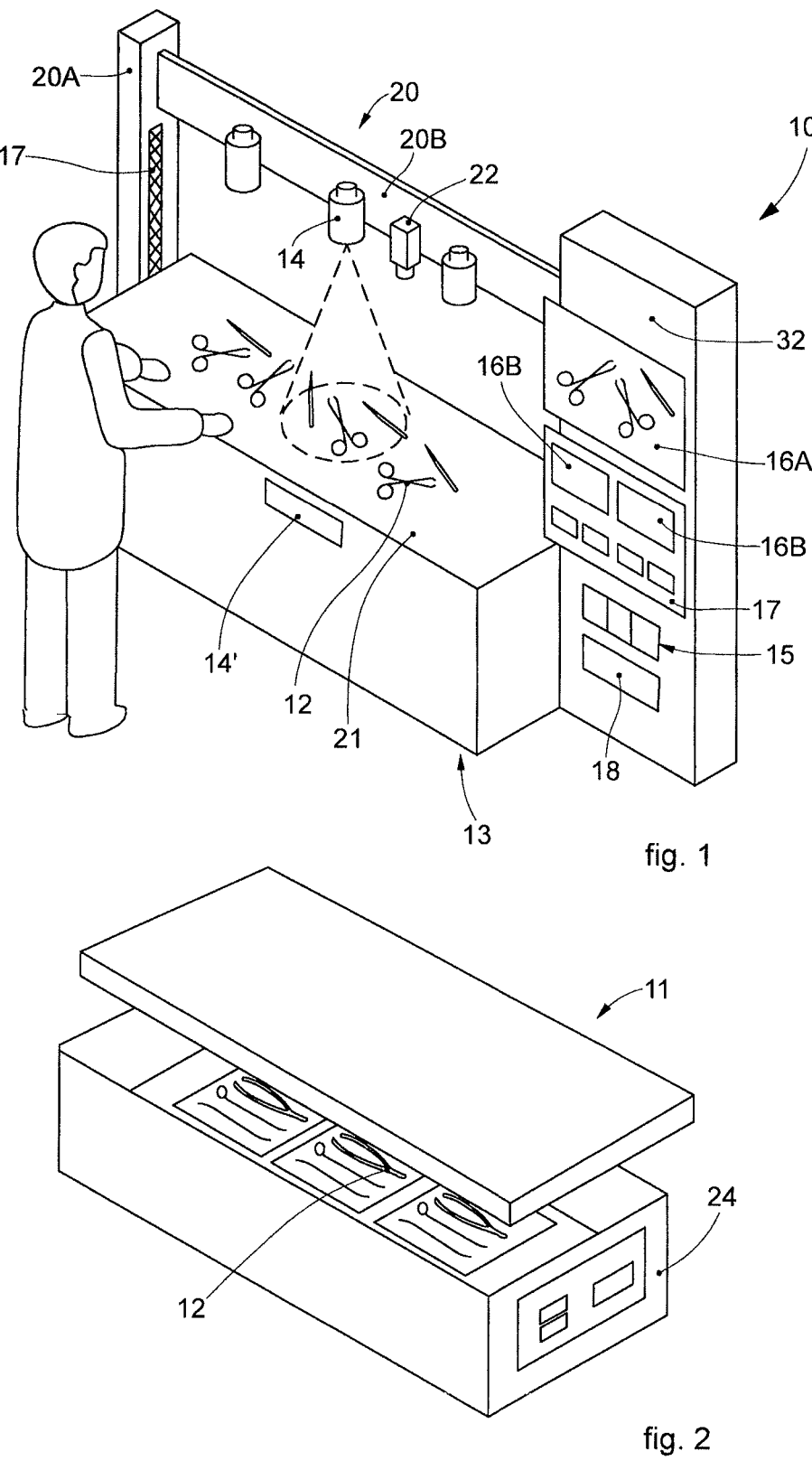
FIG. 1 is a schematic perspective view showing a workbench of an apparatus for the recomposition of a kit of surgical instruments in accordance with some embodiments described here.
FIG. 2 is a perspective view, schematic and partly exploded, showing an example of a kit of surgical instruments positioned inside their container.
Figure 3:
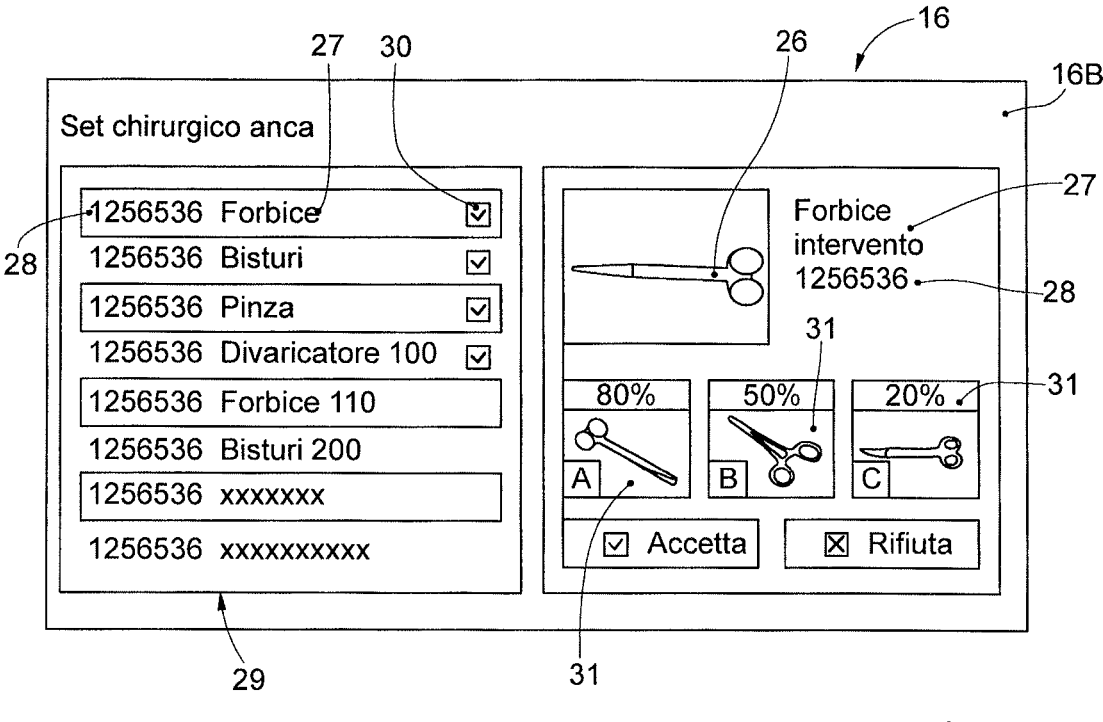
Figure 4:
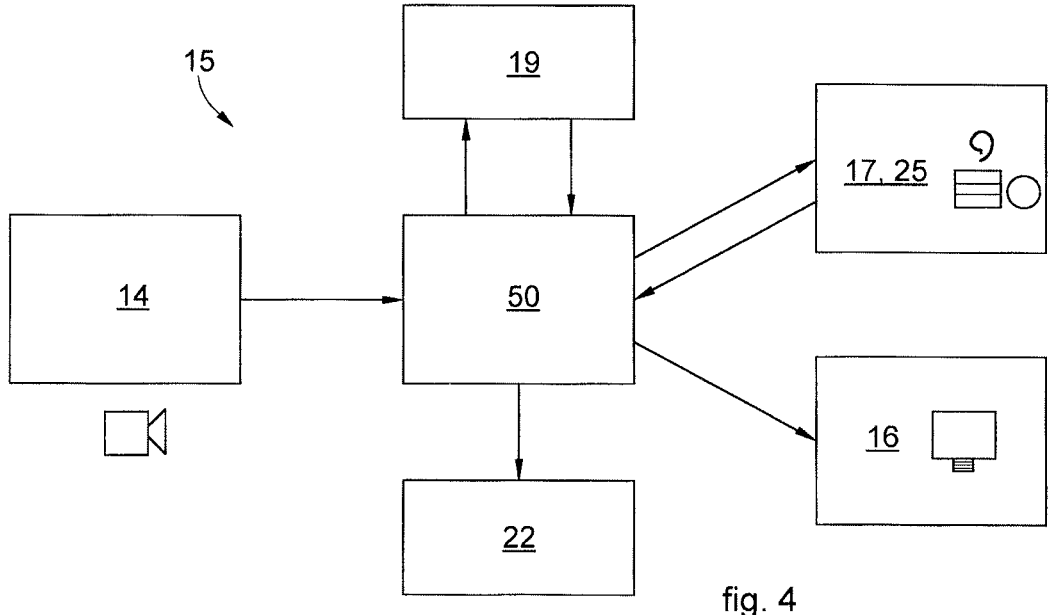

FIG. 3 schematically shows a graphic interface that can be displayed on a screen comprised in the apparatus for the recomposition of a kit of surgical instruments of FIG. 1;

FIG. 4 is a block diagram that schematically shows the flow of information exchanged during the method for the recomposition of a kit of surgical instruments in accordance with some embodiments described here.

To facilitate comprehension, the same reference numbers have been used, where possible, to identify identical common elements in the drawings. It is understood that elements and characteristics of one embodiment can conveniently be incorporated into other embodiments without further clarifications.

DESCRIPTION OF EMBODIMENTS

We will now refer in detail to the various embodiments of the invention, of which one or more examples are shown in the attached drawings. Each example is supplied by way of illustration of the invention only and shall not be understood as a limitation thereof.

For example, the characteristics shown or described insomuch as they are part of one embodiment can be adopted on, or in association with, other embodiments to produce another embodiment. It is understood that the present invention shall include all such modifications and variants.

Embodiments described here concern an apparatus 10 for the recomposition of a kit of surgical instruments 11 suitable to assist an operator in the recomposition of such kit.

The kit 11 of surgical instruments is understood to consist of a plurality of instruments 12 able to be used, as a whole, by a medical team during a particular surgical operation, each according to its own functionality.

With reference to FIG. 1, the apparatus 10 can comprise a support device 13 intended to receive the surgical instruments 12 resting on it, one or more optical detection devices 14, a data processing system 15, one or more user interface devices 16, one or more instruction acquisition devices 17.

The support device 13 comprises a support plane 21 intended to receive the surgical instruments 12 resting on it.

The support device 13 comprises a bearing structure 20, which rises vertically upward so as to be raised with respect to the support plane 21.

The bearing structure 20, in one example embodiment, shown in FIG. 1, can comprise at least one upright 20A and one crosspiece 20B.

The apparatus 10 further comprises a control column 32 which is configured to support at least the one or more user interface devices 16, and the one or more instruction acquisition devices 17. Furthermore, the electronics and components required for the correct functioning of the apparatus 10 can be integrated in the control column 32.

According to some embodiments provided here, the control column 32 can be adjacent to the support device 13, as can be seen in FIG. 1, or disposed away and separated from the latter. In the case shown, the control column 32 becomes an integral part of the bearing structure 20, since it cooperates with the upright 20A in order to support the crosspiece 20B. The latter extends, in fact, between the upright 20A and the control column 32, reciprocally connecting them in a substantially horizontal direction of development, above the support plane 21.

The bearing structure 20 is configured to support at least one selection device 22, for example a projector, of a type known in the state of the art, configured to project an adequately localized light beam toward the support plane 21 in order to selectively illuminate a determinate surgical instrument 12. In particular, this selection device 22 can be supported by the crosspiece 20B. In the embodiment shown in FIG. 1, a single selection device 22 is provided; however, it is evident that in a completely equivalent manner two or more selection devices 22 can also be provided, in order to ensure that the light beam is able to reach any point of the support plane 21 whatsoever.

In one embodiment, the selection devices 22 are configured to highlight by means of a beam of light and in a selective manner a particular surgical instrument 12 present on the support plane 21. According to one variant, there can be provided movement devices, not shown and of a type known in the state of the art, associated with the selection device(s) 22 in order to orient it/them in space, varying the angle of inclination with respect to the vertical, so as to facilitate the illumination of the desired instrument. The movement devices can comprise mechanical members, such as for example an electrically driven rack-pinion assembly.

In some embodiments, the bearing structure 20, in particular the crosspiece 20B, is also able to support possible lighting devices (not shown in the drawings), for example lamps or LED devices.

These lighting devices can be able to illuminate the support plane 21, for example in a uniform manner and without shadows.

It should be noted that such lighting devices can for example be integrated in the bearing structure 20, but also be outside the support device 13.

In some embodiments, the bearing structure 20, in particular the crosspiece 20B, is able to support the one or more optical detection devices 14.

According to one embodiment, the optical detection device 14 comprises an optical image detection device, such as a high resolution video camera of those commonly used in the industrial automation sector. By way of a non-limiting example, the embodiment of the apparatus that can be seen in FIG. 1 comprises three optical image detection devices 14, in particular equidistant along the crosspiece 20B. It is clear that other embodiments, completely equivalent, can provide a number of optical image detection devices equal to two or greater than three.

According to one embodiment, not shown, the optical detection device 14 and the selection device 22 can be integrated in a single device.

In other embodiments provided here, the support device 13 can also comprise further detection devices 14', such as for example weighing instruments and/or sensors in order to detect physical parameters, such as for example weight or also other parameters. In this case, the further detection devices 14' can be integrated in the support plane 21, as indicated by the dashed rectangle in FIG. 1.

The sensors can, for example, be impedance-meter devices, electromagnetic sensors, capacitive sensors and others still, completely equivalent to the previous ones.

In some embodiments, such as that shown in FIG. 1, the bearing structure 20 can also support one or more of the instruction acquisition devices 17, in this specific case a microphone which is integrated in the upright 20A.

In some embodiments, the data processing system 15 is a system that comprises data processing, management and storage functions.

In some embodiments, described hereafter with reference to FIG. 4, the data processing system 15 can, as a whole, be able to implement algorithms for the acquisition, management and processing of data, in addition to managing and controlling the devices 14, 14', 16, 17, 22 as above comprised in the apparatus 10 for the recomposition of the kit 11 of surgical instruments 12.

In one version, the data processing system 15 can also be able to implement an algorithm for assessing the conformity of the instruments 12.

In some embodiments, the data processing system 15 comprises a central processing unit 50, or CPU, a data storage module 19 consisting of, for example, an electronic memory, an electronic database and auxiliary circuits (or I/O) (not shown). For example, the CPU can be any form whatsoever of computer processor that can be used in the field of computing. The memory can be connected to the CPU and can be one or more of those commercially available, such as random access memory (RAM), read-only memory (ROM), hard disk, mass memory, or any other form whatsoever of digital storage, local or remote. Software instructions and data can be for example encoded and stored in the memory in order to command the CPU. The auxiliary circuits can also be connected to the CPU in order to aid the processor in a conventional manner. The auxiliary circuits can include for example at least one of: cache circuits, feed circuits, clock circuits, input/output circuits, subsystems and suchlike. A computer-readable program (or computer instructions) can determine which tasks can be done in accordance with the method according to the present description. In some embodiments, the program is a computer-readable software. The computer includes a code to generate and store information and data introduced or generated during the course of the method according to the present description.

With reference to FIG. 4, the central processing unit is indicated with reference number 50 while the data storage module is indicated with reference number 19.

In some embodiments, the data processing system 15 can be able to acquire data from the optical detection device 14, for example images from the video cameras and/or data from the weighing instruments and/or sensors 14'.

The algorithms implemented in the data processing system 15 can be able to process the data and recognize the surgical instruments 12, for example by analyzing their characteristic parameters such as sizes, shape, material and others still, in a recognition step comprised in some implementations of the method described here.

In some embodiments, the data processing system 15 can implement suitable recognition algorithms based on the recognition of one or more of the parameters as above starting from the image processing.

The recognition algorithms can for example be able to compare the data (that is, the images) with a database, for example created in a learning or initial set-up step of the method.

For example, during this learning step it can be provided to transfer into the storage module 19 one or more images for each surgical instrument 12 which the method will have to process in order to form the comparison database for the correct functioning of the recognition algorithms.

In some embodiments, the central processing unit 50 is able to send data relating to the identification carried out to the user interface devices 16.

In some embodiments, the one or more user interface devices 16 can be configured as suitable display means able to allow the central processing unit 50 to provide the operator with a graphic display relating to the identification carried out, as well as other updates relating to the ongoing recomposition process.

For example, the one or more user interface devices 16 can comprise one or more touch screens, such as for example LCD monitors attached to the control column 32. In one embodiment, a first screen can be provided, indicated with reference number 16A in FIG. 1, connected to the detection device 14, configured to show the view taken by such device. In this embodiment, other screens can be provided, indicated with reference number 16B in FIG. 1, configured to allow the operator to interact with the apparatus 10, as will be explained in greater detail below.

In some variants, not shown, the user interface devices can be configured as other suitable display means, of a type known in the state of the art or which will be developed in the future, for example not supported by the control column 32, but in any case in operational communication with the central processing unit 50. By way of a non-limiting example, the user interface devices 16 can comprise tablets, phablets, notepads, all provided with their own screen suitable for the purpose and configured to be comfortably handled by the operator.

In another variant, completely equivalent to the previous ones, the user interface devices 16 can be configured as glasses intended to be worn by the operator and which implement augmented reality techniques. In this case, the user interface device 16 will have no physical screen, but will be provided with a virtual screen visible to the operator wearing the glasses which is suitable to be configured as one of the display means as above.

With reference to FIG. 3, one example of a possible layout that can be displayed on one screen of the screens of the user interface devices 16, for example on the screen 16B, is shown.

For example, on the left side of the screen, a list is displayed of the identification data relating to a group of surgical instruments 12 comprised in the kit 11 being processed. For example, this list—which is indicated as a whole by reference number 29—comprises a numerical code and a descriptive wording for each surgical instrument 12. A distinctive sign, indicated by reference number 30, can be provided next to each wording, which can indicate the outcome of the recognition. For example, the distinctive sign 30 can be configured as a check in the event of a positive recognition, or as an "x" in the event of non-recognition.

On the right side of the screen, there can be displayed an image of the surgical instrument 12 that is being recognized as detected by the optical detection device 14, with the corresponding wording. The image and the wording are respectively indicated by numbers 26 and 27 in FIG. 3. Furthermore, under these elements, different windows can be displayed, three in the example of FIG. 3, indicated by reference number 31. These windows contain the images of as many surgical instruments 12, found by the algorithm in the management and storage module 19, and a percentage indication which is representative of the similarity between the image contained in the window and the image 26 of the surgical instrument 12 which the optical detection device 14 is framing.

In some embodiments, the data processing system 15 is able to allow a dynamic management of the data in real time.

In some embodiments, the dynamic management of the data in real time can be able to allow real-time interaction with the operator, thus following the operations carried out by the operator and at the same time providing him/her with the corresponding expected indications.

The indications provided in real time can comprise the identification of the surgical instrument 12 on which the operator is working, the check 30 of its presence on the list 29 when it has been identified, the indication relating to compliance, and more.

In one variant, the data processing system 15 can be able to allow to manage data in deferred time.

In some embodiments, the management of data in deferred time can be able to provide a waiting time linked to the indications that have to be provided during the interaction with the operator.

In some embodiments, the data processing system 15 can comprise a voice control module 25 suitably set to recognize the operator's voice.

In some embodiments, the voice control module 25 can be suitable to manage the decoding of the operator's voice, the recognition of operator commands or the response to questions shown on the screen, for example the choice between two similar surgical instruments 12.

For example, the data processing system 15 may be able to detect the configuration choices provided by the user or the deactivation of the voice control module 25 by the operator.

In some embodiments, the instruction acquisition devices 17 can be configured to receive instructions from an operator at least in a selection step in which the operator can indicate which is the surgical instrument 12 under examination among a limited group of instruments on the basis of a graphic comparison proposed on the screen 16B.

In some embodiments, at least one of the instruction acquisition devices 17 can be a device that provides a contactless interaction with the operator, for example an audio device 17 able to acquire the operator's voice instructions.

In this case, the data processing system 15 is configured to coordinate the voice recognition module 25 with the audio device 17, which are functionally correlated.

In an example embodiment, the audio device as above can be a microphone 17.

According to some variants, the one or more instruction acquisition devices 17 can be a touch screen and/or a keyboard and/or a mouse.

The apparatus 10 can be integrated and/or interfaced with one or more means 18 for connection to communication networks, such as for example cable, wireless, Bluetooth and other communication devices.

In some embodiments, the one or more means 18 for connection to communication networks allow communication between the various components of the data processing system 15, as schematically shown in FIG. 4, for example in order to exchange data and information on the kit 11 of surgical instruments 12 to be analyzed, on the operations carried out in order to manage cases where there has been an error in identification, events (for example defects in research, excessive increases in defects found) and anomalies, to update drivers and operating systems and more.

In some embodiments, the one or more connection means 18, in case of lack of connectivity, are able to provide offline data processing, for example by means of temporary storage on buffer memories.

In some embodiments, the one or more connection means 18 can be able to allow the real time connection also by means of different devices in multichannel mode, for example via a smartphone with a mobile application.

For example, the one or more connection means 18 can be able to put the apparatus 10 in communication with a centralized database in which the information relating to the management of the kits 11 coming from all the healthcare facilities connected to the same network is stored.

Some embodiments of a method for the recomposition of a kit of surgical instruments in accordance with the teachings of the present invention are described below.

Initially, the method provides that the operator positions all the washed and sterilized instruments 12 on a support plane 21 comprised in the support device 13.

Subsequently, it is optionally provided to activate possible lighting devices in order to illuminate the support plane 21 and the surgical instruments disposed thereon.

At this point, it is provided that the detection devices 14, for example the one or more video cameras supported by the crosspiece 20B, frame the support plane 21 on which the surgical instruments 12 are disposed.

It should be noted that the method can provide that the view taken by the video camera is projected in real time on a first screen 16A, for example of a large size, so as to offer the operator an adequately enlarged view of the support plane 21 and of the surgical instruments 12 disposed thereon.

At this point, the method provides a step of recognizing the instruments, in which it is provided to execute the recognition algorithm as above, in order to carry out the identification and validation of the surgical instruments 12 comprised in the kit 11.

In some embodiments, the method can provide that in the recognition step the identification of a plurality of surgical instruments 12 occurs simultaneously.

In some embodiments, the recognition algorithm implemented in the data processing system 15 can process the images detected by the detection device 14 and recognize the physical parameters of the surgical instruments 12, such as for example size, shape, color and others, in order to carry out a comparison with the images previously stored in the storage module 19.

The outcome of the recognition step is displayed by the operator directly on screen 16B. As previously described, the list 29 is dynamically compiled on such screen and the method provides to automatically place the distinctive sign 30 on each line, next to the identification code of the various surgical instruments 12.

When the image detected substantially coincides with, or can be largely superimposed on, the corresponding image present in the database, the instrument 12 is identified and its presence in the kit 11 validated.

As this gradually occurs, the method can provide that the instruments 12 already identified are distinguished by a corresponding distinctive sign 30, for example a check mark or the highlighting of the corresponding line by means of a different color, or other similar graphic indications.

If the detected image of an instrument cannot be attributed to any of the images in the database as above, a graphic indication of the failed recognition can be provided on the screen 16B. For example, in this case it can be provided to associate a different distinctive sign 30, in particular in the form of an "x", with the unrecognized instrument, or the corresponding line can be highlighted with a different color or by a flashing pattern.

In some embodiments described here, it is provided that the recognition step has a positive outcome, which means that the instrument is considered identified if the correspondence between the detected image and one of the images contained in the database is greater than a predefined threshold of confidence, for example equal to 90% or higher. If the level of correspondence between the images is lower than this threshold, then the outcome of the recognition is negative and the corresponding line of the list 29 is marked, for example with the "x".

In cases like this, for each instrument 12 not recognized, the method can provide to show the operator the image 26 detected by the detection device 14 on the screen 16B, possibly together with its name and identification code, indicated by numbers 27 and 28 in FIG. 3. In a possible embodiment, the method can provide to display for the operator, together with the image 26 relating to the identification carried out, some windows 31, each representing a surgical instrument similar to the one visible in the image 26, together with the indication of a respective degree of compatibility between the instrument visible in the window and the one shown in the image 26. In this way, the method provides to offer the operator the possibility of indicating which instrument, among the choices suggested in the windows 31, is the one shown in the image 26.

In one example embodiment, the number of windows 31 is smaller than 5, in particular equal to 2 or 3.

According to some variants, the number of windows 31 proposed to the operator for inspection increases as the degree of compatibility of the instruments shown in the windows 31 with that shown in the image 26 decreases.

In the example of FIG. 3, the first window 31 shows an instrument that has a degree of compatibility with the instrument visible in the image 26 of 80%, the second window 31 shows an instrument that has a degree of compatibility with the instrument visible in the image 26 of 50%, and the third window 31 shows an instrument that has a degree of compatibility with the instrument visible in the image 26 of 20%.

According to some embodiments provided here, the method therefore provides that the operator can choose which instrument is the one shown in the image 26, among those shown in the windows 31 proposed.

In one version, the operator can communicate the choice by means of voice commands, detected by the microphone 17 and processed by the module 25. For example, he/she can indicate the letter (A, B or C in the example of FIG. 3) that distinguishes the window 31 containing the same instrument 12 as the image 26.

In one variant, the method can provide that in the selection step, the operator can confirm the identification also by means of commands entered directly on the screen 16B, of the touch screen type.

In another variant, the method can provide that in this step the operator can confirm the choice also by means of a keyboard and/or mouse.

In one variant, the method can provide to further check the correctness of the kit 11 of surgical instruments 12 formed, by comparing the total weight of the surgical instruments 12 positioned on the support plane 21 (detected by the weighing instruments 14') and intended to make up the kit 11, with the total theoretical weight of the kit 11 of surgical instruments 12. Once the average weight of a single instrument is known, this check also allows to check that the kit comprises the number of instruments expected, or possibly infer how many instruments are missing on the basis of the difference between the total weight expected and the one measured.

In one variant, the method can provide a step of evaluating the conformity of the instruments 12 by processing the images 26 acquired.

In some embodiments of the variant, in order to assess the conformity of the instruments 12, the presence or absence of defects due to chemical, thermal and/or physical influences can be assessed, such as for example patinas from organic residues, patinas from residues of process chemical substances, patinas from water stains due to limescale, patinas from silicates and other mineral alloys, oxidation deposits, patinas/color alteration/fading and colored deposits from plasma, pitting corrosion, corrosion due to wear, corrosion due to friction, surface corrosion, rust induced by external sources, tension cracks and others.

In some embodiments, for example once the recognition of all the instruments 12 disposed on the support plane 21 has been completed with a positive outcome, the method can provide to communicate to the operator which instrument 12 to take, one at a time, highlighting it by means of a light signal emitted by the selection device 22, for insertion into the container 24. It should be noted that these embodiments can provide to selectively highlight the surgical instruments 12 one after the other, according to the pre-set order of removal, even while the recognition step is in progress. In this way, since the recognition step automatically proceeds at high speed, the method according to the present invention can provide to selectively highlight the surgical instruments that have already been recognized and whose presence in the kit 11 has already been validated, while the step of recognizing other surgical instruments 12 not yet recognized proceeds in parallel, so as to reduce the overall times of the method for the recomposition of the kit 11 of surgical instruments 12.

According to variants of implementation of the recomposition method according to the present invention, a self-learning function can be provided, thanks to which the method is able to refine the recognition step and/or the step of selection by the operator. For example, if the analysis of the processed data shows that for a certain surgical instrument 12 a choice is always presented to the operator, and he/she always selects the same window 31, the algorithm will be able to take this into account, for example by suitably increasing the percentage that indicates the level of compatibility of that instrument 12, so that the level of confidence exceeds the predefined threshold, that is, preventing proposing the choice to the operator. In one variant, the self-learning function can also be based on the data processed by the data processing system 15 that governs a method and an apparatus for the recomposition of a kit 11 of surgical instruments 12 in other structures. In this case, a central data management and coordination server is provided, which communicates with the data processing systems 15 of the different structures, which are connected to each other in order to form a network. In this variant, recurrent results of the data processing in one structure can be used by the algorithm to refine the recognition and selection steps in another structure.

Some embodiments can provide the execution of various steps, passages and operations, as described above. The steps, passages and operations can be carried out with instructions executed by the central processing unit 50 which cause the execution of certain steps by a general-purpose or special-purpose processor. Alternatively, these steps, passages and operations can be executed by specific hardware components that contain hardware logic to perform the steps, or by any combination of components for programmed computers and personalized hardware components.

Embodiments of the method in accordance with the present description can be included in a program for computers that can be stored in a computer-readable mean that includes the instructions that, once performed by the apparatus 10 suitable to implement the method for the recomposition according to the present invention, determine the execution of the method discussed here. In particular, elements of the method according to the present description can be given as machine- or processor-readable means to store the instructions which can be carried out by the machine or processor. The machine-readable means can include, without being limited to, floppy disks, optical disks, CD-ROM and optical-magnetic disks, ROM, RAM, EPROM, EEPROM, optical or magnetic cards, propagation means or other types of machine- or processor-readable means suitable to memorize electronic information. For example, the method according to the present description can be downloaded as a computer program that can be transferred from a remote computer (for example a server) to a requesting computer (for example a client), by means of data signals produced with carrier waves or other propagation means, via a communication connection (for example a modem or a network connection).

It is clear that modifications and/or additions of steps or parts may be made to the method for the recomposition of a kit 11 of surgical instruments 12 and to the corresponding apparatus 10 for the recomposition as described heretofore, without departing from the field and scope of the present invention.

It is also clear that, although the present invention has been described with reference to some specific examples, a person of skill in the art shall certainly be able to achieve many other equivalent forms of method for the recomposition of a kit 11 of surgical instruments 12 and of the corresponding apparatus 10 for the recomposition, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. A method for the recomposition of a kit of surgical instruments, comprising:

disposing a plurality of surgical instruments on a support plane comprised in a support device;

acquiring an image of said plurality of surgical instruments disposed on said support plane by means of at least one optical detection device;

recognizing each surgical instrument by processing the acquired image using a data processing system including a computer processor by comparing said acquired image with comparison images contained in a storage module of the data processing system; and graphically displaying on a user interface an outcome of the recognition step, wherein this outcome is positive if the acquired image can be superimposed at least partly on one of the comparison images contained in said storage module with a level of confidence higher than a predefined threshold, wherein if the outcome of the recognition step is negative, said level of confidence being lower than said predefined threshold, a selection step is provided, in which the operator indicates through an instruction acquisition device which is the surgical instrument being examined among a limited group of surgical instruments on the basis of a graphic comparison proposed on a screen comprised in said user interface, wherein said selection step can provide to show the operator the acquired image of the surgical instrument acquired by said at least one optical detection device and some windows, each representing a surgical instrument similar to the one visible in said acquired image, together with an indication of a respective degree of compatibility, expressed as a percentage, between the surgical instrument visible in the respective window and the one shown in said image.

2. The method as in claim 1, wherein said selection step provides to receive voice instructions from the operator to communicate the window containing the selected surgical instrument.

3. The method as in claim 1, further comprising illuminating said support plane by means of one or more lighting devices and guiding the operator in removing the surgical instruments from said support plane in order to insert the surgical instruments in a corresponding container intended to contain the kit of surgical instruments by selectively highlighting the surgical instruments, one at a time, by means of a light signal emitted by at least one selection device.

4. The method as in claim 1, wherein the graphic display step provides to show the operator a list of identification data relating to the surgical instruments of the kit of surgical instruments, and associating a distinctive sign with each surgical instrument on the list, said distinctive sign reflecting the outcome of said recognition step.

5. The method as in claim 1, wherein said predefined threshold is a value greater than 80%, where this percentage indicates the degree to which said acquired image can be superimposed on one of the comparison images contained in said storage module.

6. A non-transitory computer-readable medium containing program instructions that can be executed by a computer in order to implement a method for the recomposition of a kit of surgical instruments, said program instructions comprising the steps of the method according to claim 1.

\* \* \* \* \*